(12) United States Patent
Aston

(10) Patent No.: US 8,652,164 B1
(45) Date of Patent: Feb. 18, 2014

(54) RAPID USE FIELD TOURNIQUET

(76) Inventor: Kevin Aston, Altoona, WI (US)

( * ) Notice: Subject to any disclaimer, the term of this patent is extended or adjusted under 35 U.S.C. 154(b) by 252 days.

(21) Appl. No.: 13/100,598

(22) Filed: May 4, 2011

(51) Int. Cl.
*A61B 17/00* (2006.01)

(52) U.S. Cl.
USPC .......................................................... 606/203

(58) Field of Classification Search
USPC .......................................................... 606/203
See application file for complete search history.

(56) References Cited

U.S. PATENT DOCUMENTS

| 6,746,470 B2 | 6/2004 | McEwen et al. | |
| 7,320,699 B2 * | 1/2008 | Kirchner | 606/203 |
| 7,947,061 B1 * | 5/2011 | Reis | 606/203 |

OTHER PUBLICATIONS

M2 INc., RMT—Instructions, RMT Racheting Medical Tourniquet, http://www.m2inc.biz/military/RMT-Instructions.htm, Aug. 11, 2010, USA.

* cited by examiner

*Primary Examiner* — Melanie Tyson
(74) *Attorney, Agent, or Firm* — Anthony J. Bourget

(57) ABSTRACT

The tourniquet is a lightweight, compact, and highly efficient device that can be used to assist in the control of life threatening extremity hemorrhage. The tourniquet utilizes a ratchet mechanism to obtain a mechanical advantage when tightening the tourniquet. A ratchet assembly is located a distance away from a strap end of the tourniquet and overlays a contiguous portion of the strap, allowing the tourniquet to be tightened while minimizing pinch, and further includes an elongated ratchet lever for ease of use, requiring minimal, if any, fine motor skills. The design also includes an indicator region for assistance in use of the device and a sealed and tapered strap-end with indicator for efficient use.

12 Claims, 10 Drawing Sheets

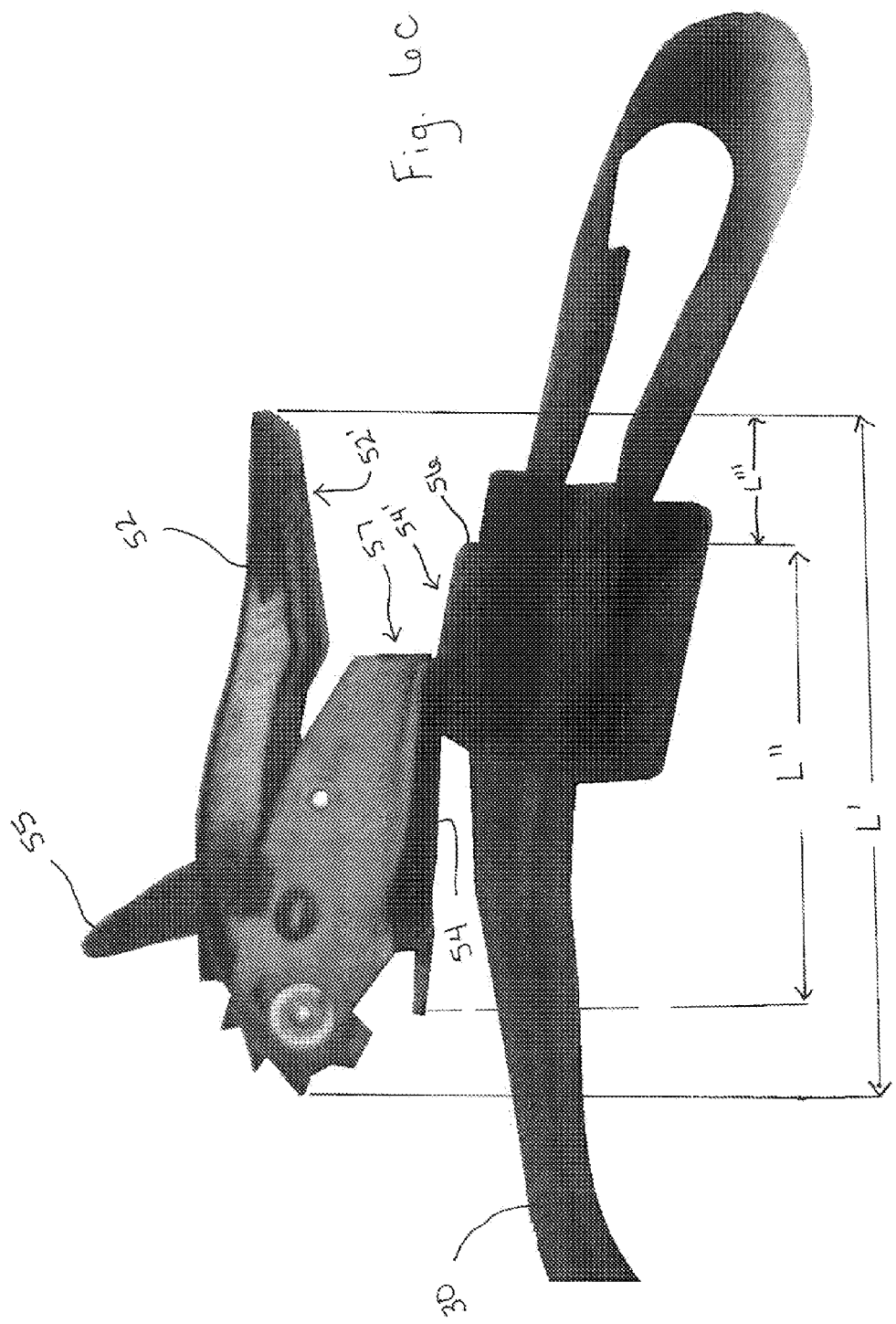

RAPID USE FIELD TOURNIQUET

BACKGROUND OF THE INVENTION

1. Field of the Invention

The present invention relates generally to tourniquets and tourniquets that may be quickly deployed and tightened with a ratchet mechanism.

2. Background Information

Uncontrolled hemorrhage from an extremity is one of the leading causes of death in military combat and a significant problem in the civilian pre-hospital environment. This uncontrolled hemorrhage from an extremity is a preventable cause of death.

US Army research (Calkins et al, "Evaluation of possible battlefield tourniquet systems for the far-forward setting", Military Medicine Vol. 165, 5:379, May 2000) defines the need for a light, compact, yet rugged tourniquet for far-forward battlefield use. Exsanguination can be reduced through the use of tourniquet technology if properly designed and implemented. The ratchet tourniquet design was deemed superior in performance, but lacked characteristics that allowed the tourniquet to have optimal effectiveness. The key features required for optimal performance of a tourniquet include: easy and quick placement, compact for storage and carrying by a soldier, simplicity of design, ruggedness, and ability to utilize the tourniquet for all extremities (one-handed use).

The increased use of battlefield tourniquets in the recent Iraq/Afghanistan wars has led to increasing acceptance of tourniquet use in the civilian pre-hospital setting. This acceptance is based on scientific research that has shown tourniquets to be useful and dispels previously held misconceptions about tourniquets (Kragh et al, "Practical use of emergency tourniquets to stop bleeding in major limb trauma", J Trauma, 2008; 64:S38-S50). While the prior art has provided examples of features of tourniquets, there is always room for further improvement.

SUMMARY OF THE INVENTION

The novel design of the present tourniquet overcomes problems encountered with previous tourniquets utilizing a mechanical closure/ratchet device.

For a device such as the present field tourniquet for rapid use, a/k/a Rapid Field Tourniquet™ or RFT™, to be successfully utilized in the field or pre-hospital environment, it ideally has several characteristics.

1. Simple to operate in all conditions
2. Rugged
3. Reliable
4. Lightweight
5. Compact Size
6. Able to be applied to self
7. Able to be applied one handed
8. Able to be applied to trapped extremity
9. Require no or minimum fine motor skill
10. Provide a means to document application time
11. Cost effective Numerous prior art tourniquets exist using various means to control bleeding. This includes mechanical closures, elastics, pneumatic bladders, and loop and windlass.

The present invention provides a tourniquet utilizing a strap and mechanical ratchet assembly mechanism to control bleeding from an extremity. This invention addresses the short comings of previous designs utilizing a ratchet mechanism/mechanical closure and strap.

In order for a tourniquet to control massive bleeding from an extremity it must exert enough circumferential pressure to occlude arterial blood flow. There are many means by which this is possible. The Rapid Field Tourniquet (RFT) uses a 2 stage process to achieve the required force to stop the bleeding.

The first stage is accomplished by tightening the strap around the limb. This will exert some degree of compression on the underlying tissue and blood vessels. This first stage also prepares the Rapid Field Tourniquet (RFT) for the second stage of compression which utilizes a ratchet mechanism.

The second stage utilizes a ratchet for mechanical advantage to achieve the required compression to help control bleeding from the extremity.

Prior art utilizing a ratchet or other means of mechanical closure place the ratchet or mechanical closure at the end of the strap. When the ratchet or mechanical closure is engaged, the device at the end of the strap becomes the leading edge where constriction occurs. In the previous designs this creates numerous problems which make the tourniquet ineffective. This is described in (U.S. Pat. No. 6,746,470 McEwen et al Jun. 8, 2004).

The previous designs that utilize the ratchet or mechanical closure system in this manner cause severe pain, pinching, friction between strap and limb, and entanglement of tissue/skin in the ratchet mechanism. The bulk of these tourniquets place the ratchet or mechanical closure in the traditional location at the end of the strap. Unfortunately placing the ratchet in the traditional position creates problems and is not effective.

The Rapid Field Tourniquet's design departs from typical devices. The Rapid Field Tourniquet utilizes a ratchet/mechanical closure placed on top of the strap and away from the leading edge of the strap, and utilizes an enlarged lever and other features for improved use.

This design overcomes several problems encountered as described in (U.S. Pat. No. 6,746,470 McEwen et al Jun. 8, 2004). By placing the ratchet mechanism/mechanical closure on top of the strap (overlaying the strap) and away from the ends the following problems are minimized or overcome:

1. No or minimal pinching occurs at the leading edge because the ratchet/mechanical closure is not at the end of the strap.

2. The ratchet/mechanical closure sits on top of a wide strap. This prevents or minimizes tissue/skin from becoming entangled in the ratchet/mechanical closure.

3. The ratchet/mechanical closure sits on top of a wide strap. This prevents or minimizes friction from occurring between the closure mechanism and underlying tissue/skin.

4. The ratchet/mechanical closure sits on top of a wide strap. This creates a simple and efficient system to rapidly apply the tourniquet with only gross motor skills and one handed if needed.

The present invention is directed toward a tourniquet using the above design together with having readily assessable features such as an extended ratchet lever for ease of use in stressful situations. The extended ratchet lever is broadened for improved grasping or hooking with a single thumb or forefinger or the side of a hand or glove. A further aspect of the invention includes use of an indicator placed on the extended ratchet lever. The indicator includes a color that is in contrast to the ratchet lever and that is also in contrast to the general color of the tourniquet. A further aspect includes the tapering and sealing of a distal end of the tourniquet strap. Such tapering and sealing accommodates for efficient handling and re-threading of the strap in an emergency situation. The tapered and sealed distal end is especially useful in cases where the tourniquet must be unthreaded and subsequently fed under or about an entrapped limb for wrapping around the limb (as opposed to where the tourniquet is simply placed over the end of the limb already looped through the buckle, such as sliding the tourniquet over the extremity of the injured limb). Further, the tapered and sealed distal end may also include an indicator.

The above summary of the present invention is not intended to describe each illustrated embodiment, aspect, or every implementation of the present invention. The figures and detailed description that follow more particularly exemplify these and other embodiments and further aspects of the invention.

BRIEF DESCRIPTION OF THE DRAWINGS

The invention may be more completely understood in consideration of the following description of various embodiments of the invention in connection with the accompanying drawings, in which:

FIG. 6C is a side view of a ratchet feature of the present invention.

DETAILED DESCRIPTION OF THE INVENTION

A specific embodiment illustrated is not intended to be exhaustive or to limit the invention to the precise form disclosed. It is chosen and described in order to explain the principles of the invention and its application and practical use, and thereby enable others skilled in the art to utilize the invention.

The preferred embodiment is an improvement of the traditional ratchet tourniquet used to stop exsanguination from the extremities. Most currently used ratchet tourniquets have the ratchet assembly located at the end of the strap. In the preferred embodiment of the invention, the ratchet assembly is located a distance away from the strap end and overlays a contiguous portion of the strap, allowing the tourniquet to be tightened without the pinch point inherent in most current designs, and further includes an elongated ratchet lever.

Figure 1:
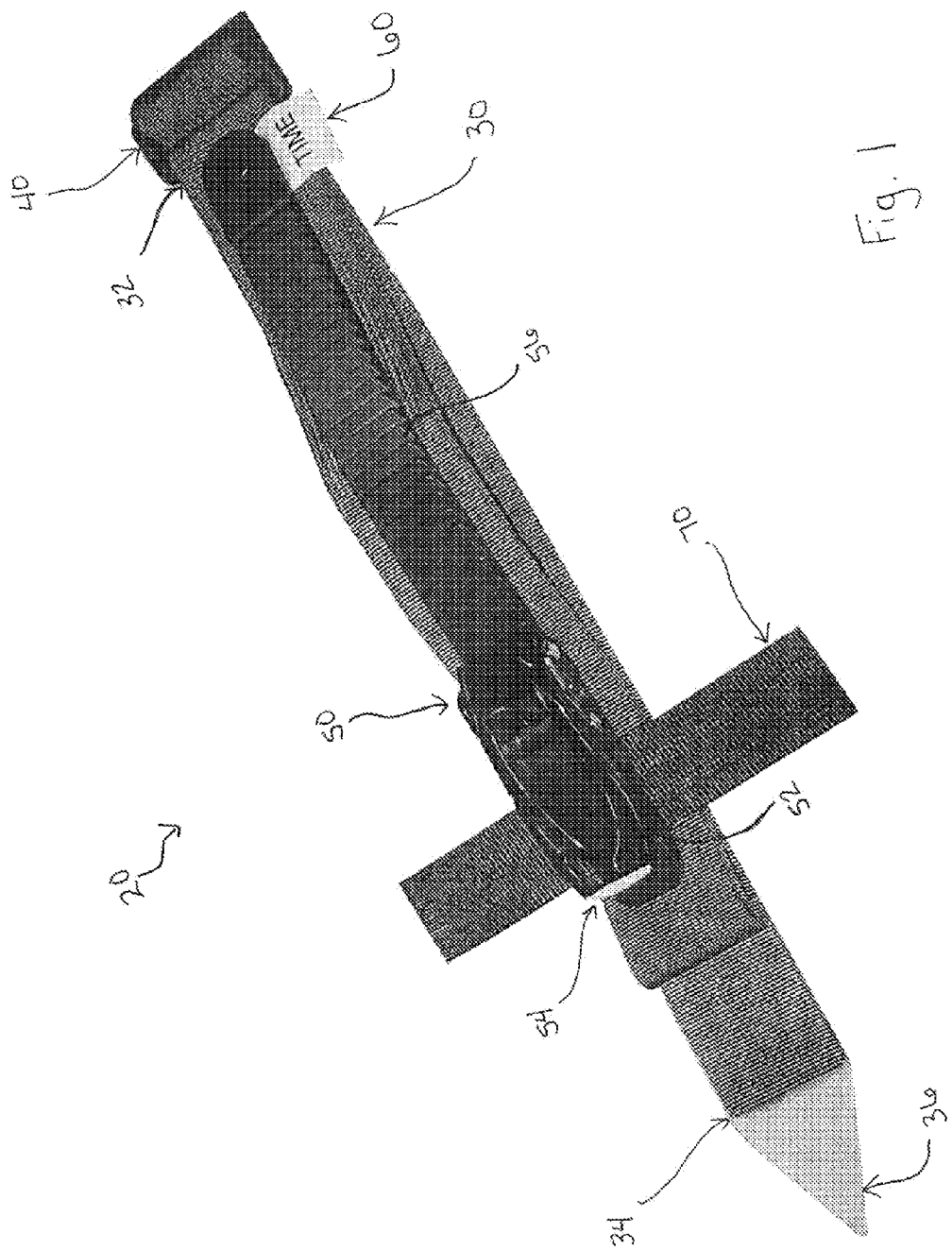
FIG. 1 is a perspective view of a tourniquet embodying the present invention.
Figure 7:
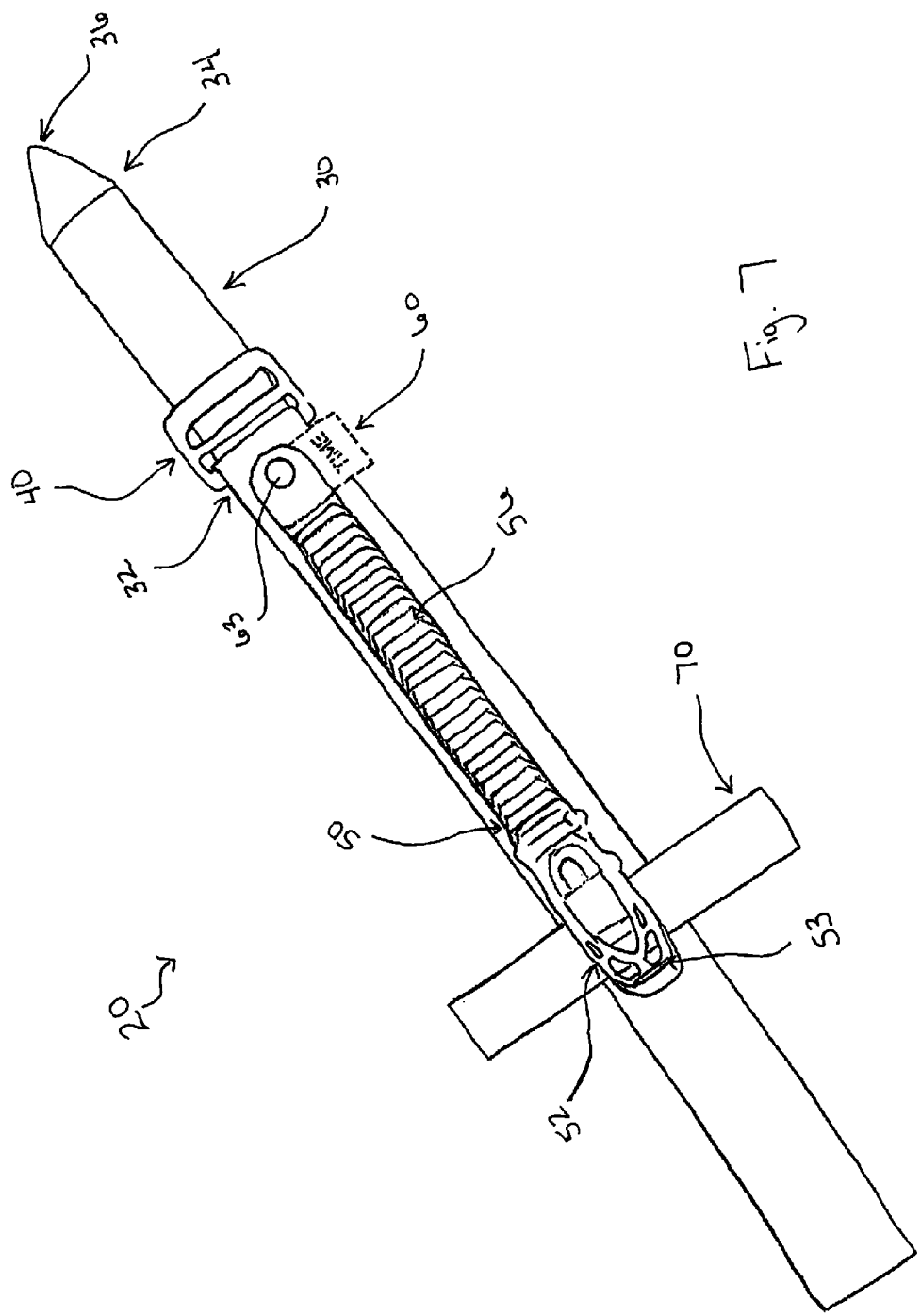
FIG. 7 is a perspective view of a tourniquet embodying the present invention.

Referring to FIGS. 1 and 7, the tourniquet device of this invention as illustrated in the various embodiments herein is generally designated as 20. The invention has a strap 30, with a proximal end 32 and a distal end 34. The proximal end 34 of the strap 30 is attached to the buckle, generally designated as 40. At the distal end 34 of strap 30 is a sealed and tapered polymeric end 36 which allows for ease of use in threading buckle 40. The ratchet assembly, generally designated as 50, is attached to strap 30 some distance from the buckle attachment of proximal end 32 of strap 30. At the proximal attachment point for ratchet assembly 50, on strap 30, is a time indicator label, designated as 60 and labeled with the notation "TIME" on which a time of use can be written. At the distal attachment point for ratchet assembly 50 on strap 30 is a retainer wrap 70. For illustrative purposes FIG. 1 shows strap 30 wrapped back under itself such that tapered end 36 is projecting in the same general direction as is lever 52. FIG. 7 also shows strap 30 wrapped back or folded under itself such that tapered end 34 is projecting in a direction opposite lever 52.

Figure 2:
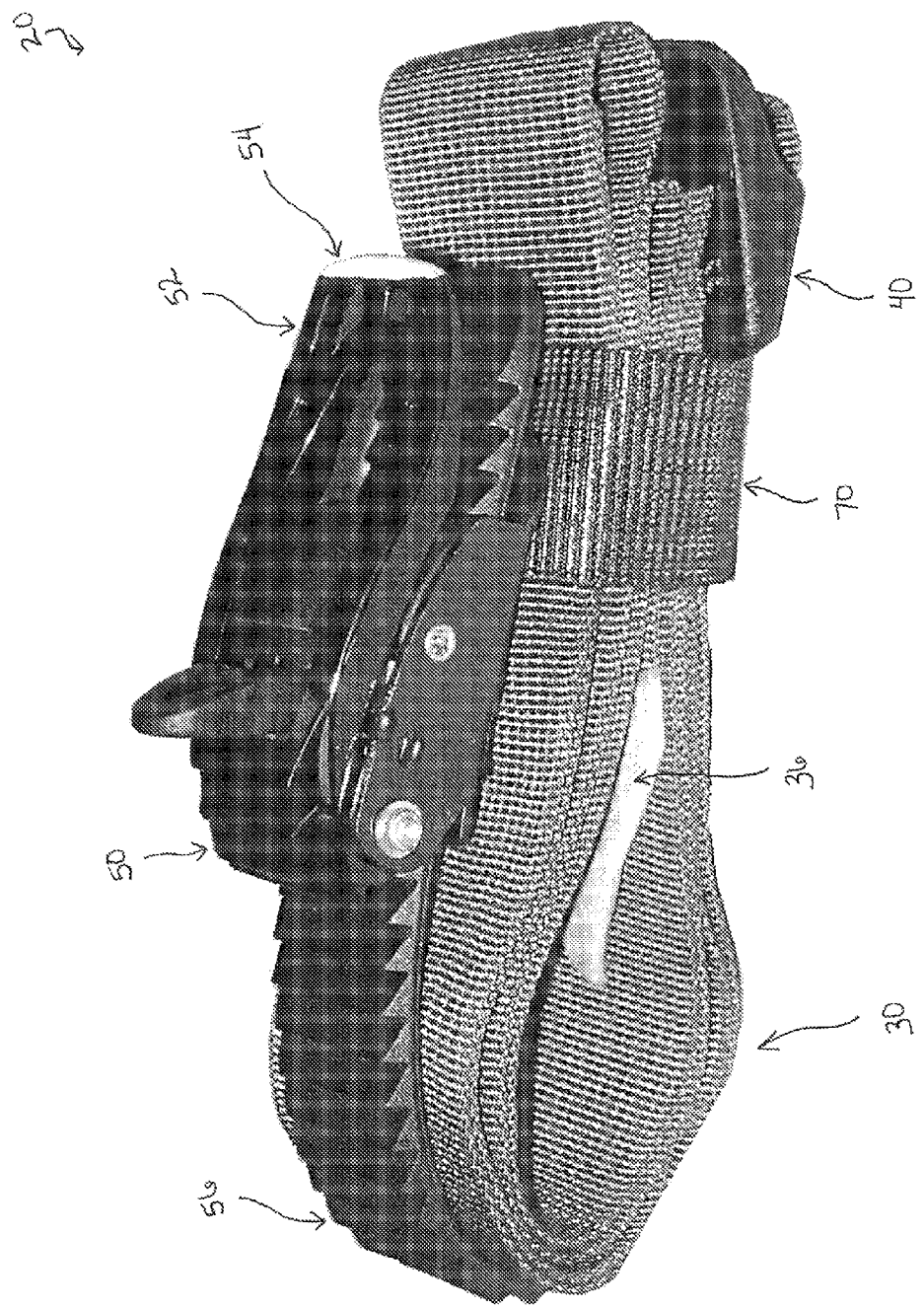
FIG. 2 is a side perspective view of the tourniquet shown in FIG. 1 where the tourniquet is wrapped for transport or storage.
Figure 3:
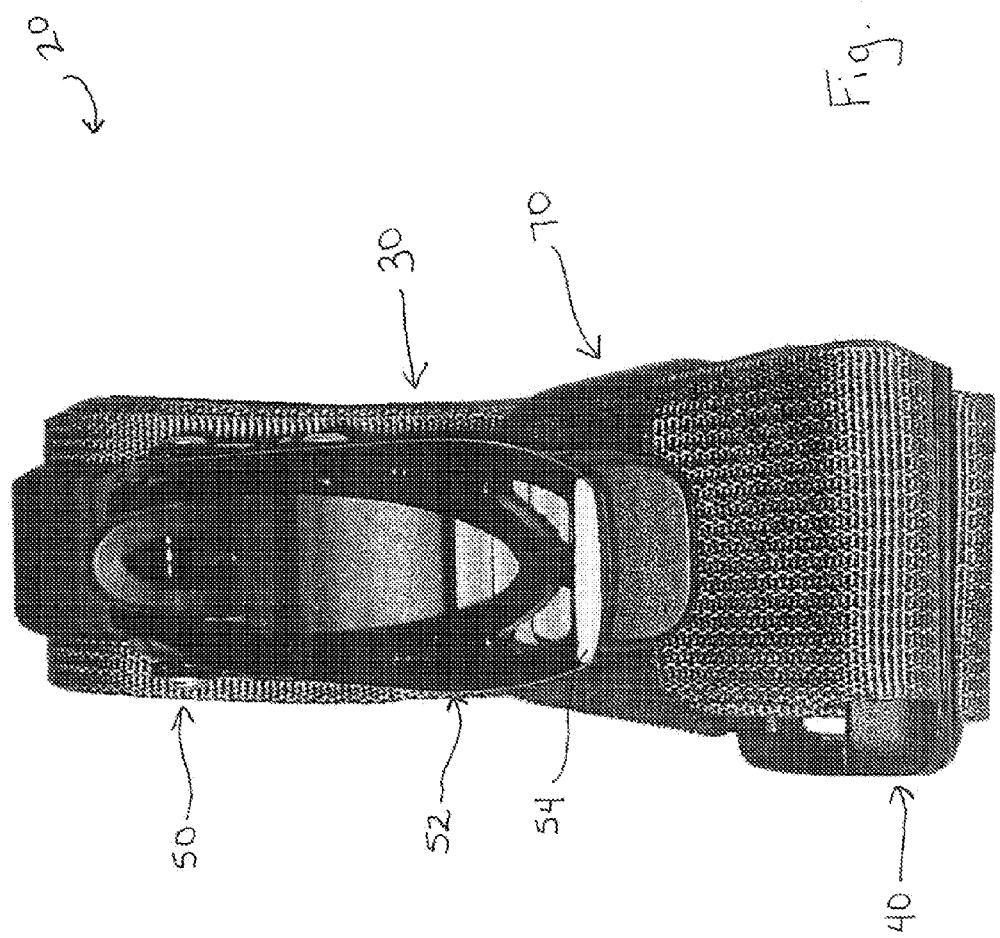
FIG. 3 is a front end perspective view of the tourniquet of FIG. 2.

Referring to FIGS. 2 and 3, when not in use, tourniquet 20 is wrapped with retainer wrap 70 for compact and easy storage.

Figure 4:
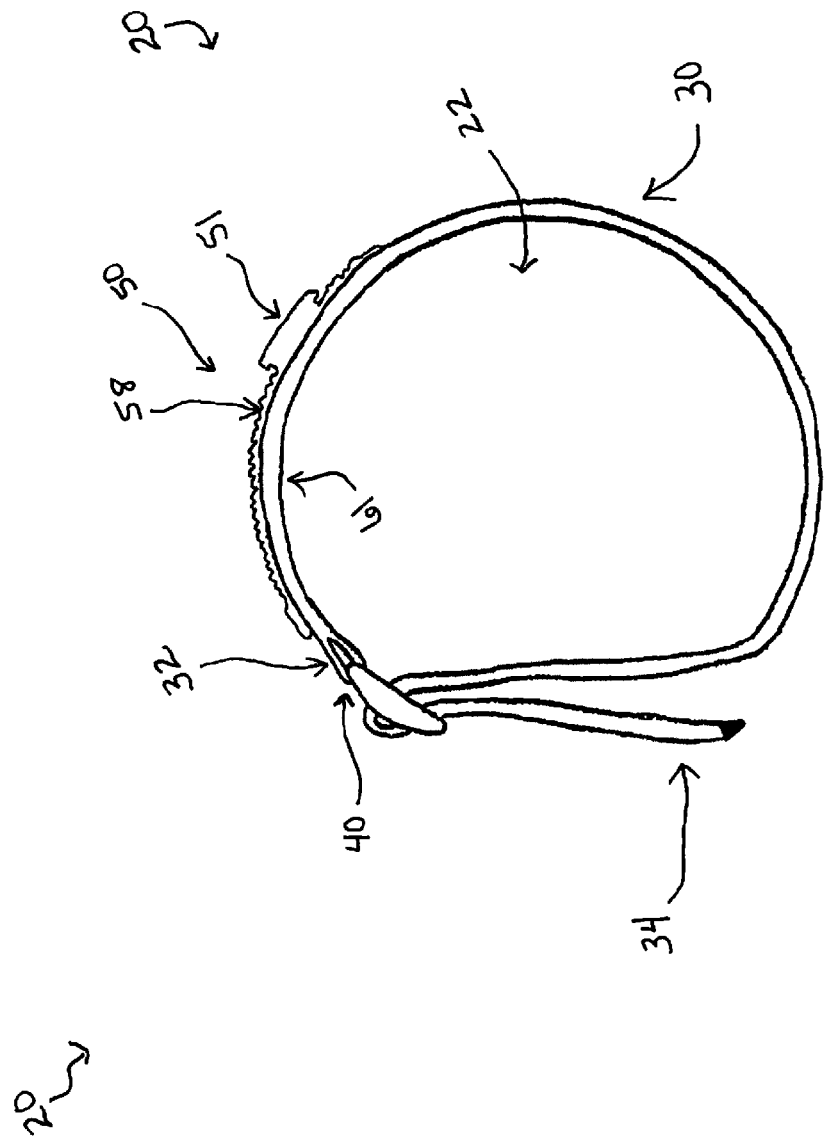
FIG. 4 is a side view of the tourniquet of FIG. 1 in an unwrapped position.
Figure 5:
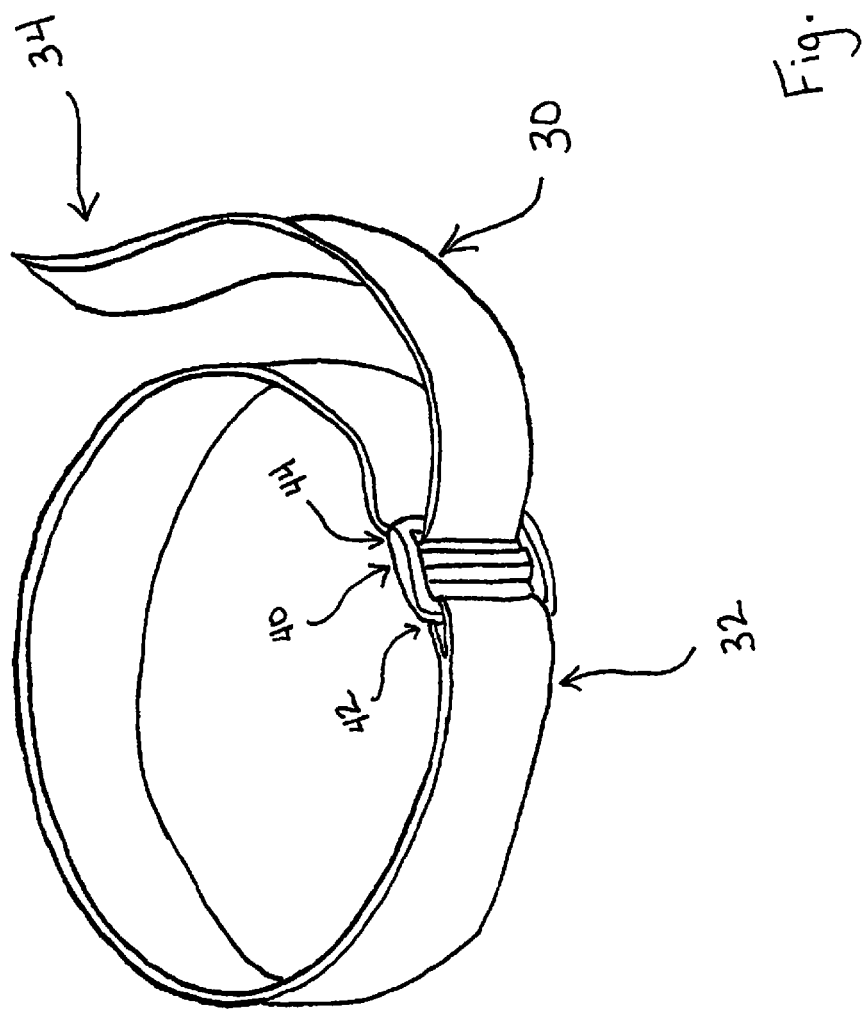
FIG. 5 is a perspective view of the tourniquet of FIG. 4.

Referring to FIGS. 4 and 5, when an injured extremity is able to be accessed without having to un-loop distal end 34 of strap 30 from buckle 40, tourniquet 20 can commence the first stage of tightening strap 30 around the limb without the buckle looping preparation step. It may be appreciated that tourniquet 20 may be placed around a limb where constricting loop 22 surrounds the limb. A user may then pull distal end 34 of strap 30 for the first stage of tightening. The design allows tourniquet 20 to be utilized even if the injured limb cannot be accessed at the end of the extremity by slipping the constricting loop over the extremity. Where a limb is entrapped the device must be un-looped since there is no access over the end of the limb. By un-looping strap 30 from buckle 40, tourniquet 20, or at least one end of strap 30, can slide under the extremity and be re-looped before the first stage of tightening strap 30 against the limb. The sealed and tapered polymeric end 36 of distal end 34 of strap 30 allows for a semi-rigid end to be fed under the injured extremity, and such action may occur with one hand. Since distal end 34 is tapered and treated with a polymer material, it may be more easily threaded within buckle 40. Preferably the polymer material is also an indicator and having a color in contrast with the remaining color of strap 30. Preferably the indicator color is yellow. Colors or shades of red or pink should be avoided since the same would have a lesser effect in these situations where blood present. An indicator placed at the end of distal end 34 allows a user to more swiftly locate the end of strap 30 for faster insertion of strap within buckle 40.

Figure 6A:
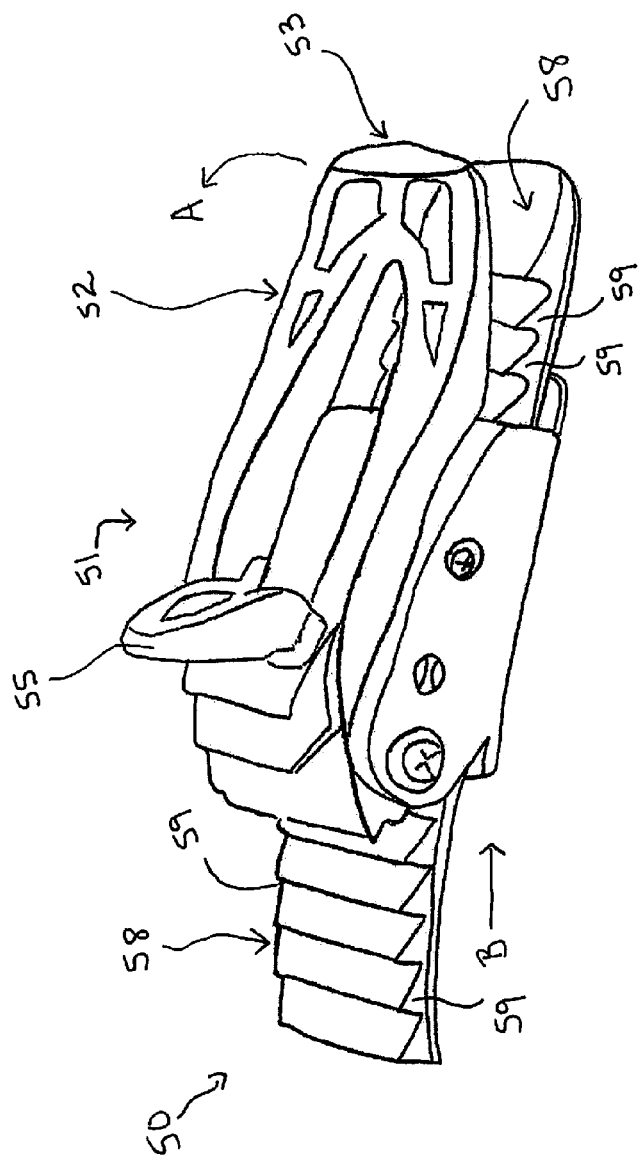
FIG. 6A is a perspective view of a portion of the ratchet assembly separate from the tourniquet.
Figure 6B:
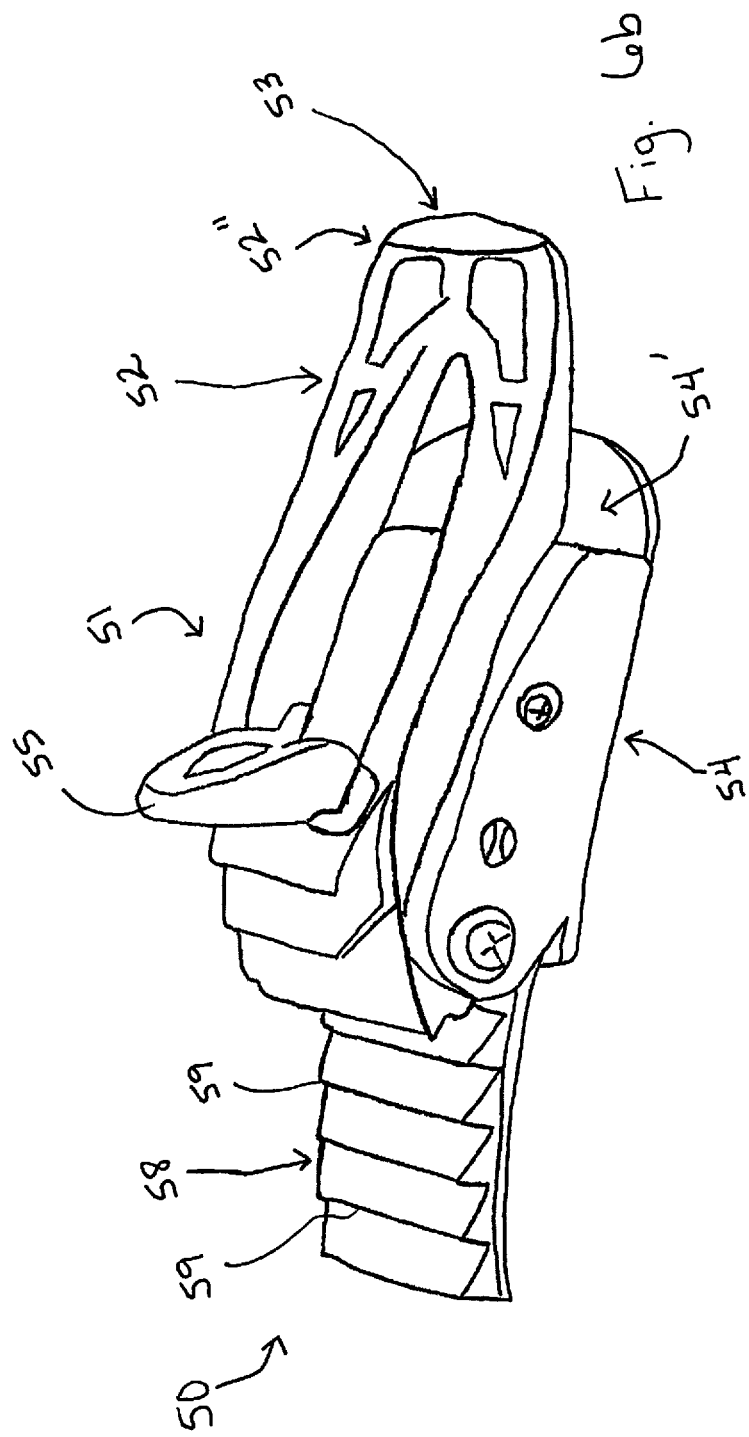
FIG. 6B is a perspective view of a portion of the ratchet assembly separate from the tourniquet and with a portion of the ratchet strip retracted.

Referring to FIGS. 6A, 6B, and 6C, ratchet assembly 50 shows a ratchet 51 having a lever 52 configured with a ratchet base 54 which receives a ratchet strip 58 having a series of gears 59. Lever 52 is depicted in a generally resting position. When lever 52 is lifted in the direction of Arrow A, ratchet strip 58 is ratcheted through ratchet 51 in the direction of Arrow B as is commonly understood. Release tab 55 allows a user to release the mechanism so that the strip 58 may travel in the direction opposite arrow B. Lever 52 is enlarged such that it reduces the need for fine motor skills to operate. With reference to FIG. 4, ratchet strip 58 overlays a contiguous portion 61 of strap 30. It may be appreciated that strap 30 may form a constricting loop 22 even where strip 58 is removed from ratchet 51.

In one aspect, ratchet base 54 includes a base extension 54'. Ratchet 51 may be secured to strap 30 in many ways. In one aspect ratchet 51 is secured to strap 30 by using a fastener, such as a rivet that may be inserted through base extension 54' (See FIG. 6b). It may be appreciated that a single fastener, such as a rivet or other fastener may be used to secure ratchet 51 to strap 30. Ratchet strip 58 is also connected to strap 30. In one aspect strip 58 is connected by using a fastener, such as a rivet 63 that may be inserted through strip 58 and into strip 30. It may be appreciated that other types of fasteners may be used for such connection.

Lever 52 extends past base terminal end 56. In one aspect lever 52 has a length L' that is greater than a length L" of ratchet base 54. Lever 52 extends a length L''' past base terminal end 56. Preferably lever 52 extends past shoulder 57 such that a user may position more than one finger upon an underside 52' of lever 52 when lever 52 is generally in a resting position. Preferably a user will be able to apply more than one finger to underside 52' when lever 52 is generally in a resting position as shown in FIG. 6c. More preferably a user will also be able to apply the side of the hand or palm to the underside 52' of lever 52. In one aspect lever 52 extends past shoulder 57 at least ½ inch, and preferably greater than ¾ inch. In one aspect terminal end 56 may extend past shoulder 57 ½ inch. When lifted, lever 52 may receive two or more fingers, or the side of a hand or palm, so that an operator may grasp or push securely upon lever 52 and impart a strong tightening or ratcheting force.

Figure 8:
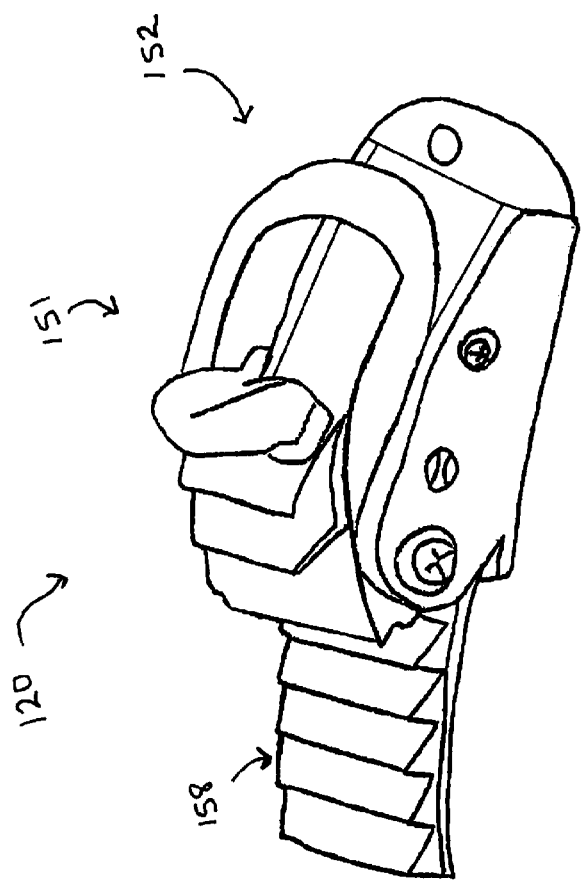
FIG. 8 is a perspective view of a prior art ratchet used in earlier designs.

Lever 52 also has a colored indicator 53 that improves the ease of identification and use in stressful or emergency medical situations. In designs of the prior art, for instance the prior art device 120 shown in FIG. 8, where a lever 152 was not enlarged and/or where no indicator was present, a user, especially under stress, may tend to be confused as to which side of the ratchet 151 was the side to lift for operation. The prior art ratchet assembly shown in FIG. 8 has been used in conjunction with a ratchet strip 158 which overlays a contiguous portion of a tourniquet strap. In some designs, where a string or small pulling cord may be present, the situation was also troublesome since use of a cord is a disadvantage since a string or cord must be grasped with fingers (typically index finger and thumb), an action requiring grip and dexterity. The same is true with a twisting stick/windlass, or turning a dial as in other designs. Further, in some stressful situations, grasping a string or even a small-profiled lever is troublesome. Often a user will be wearing gloves, or will have cold fingers or other circumstances making operations difficult. The present invention, however, which utilizes an enlarged lever and which has a clear indicator 53, and which may be manipulated with multiple fingers or the side or palm of the hand (or glove), provides for ease and a more rapid application. The device may be applied by a single person and may be applied by one's self. Lever 52 is operable with gross motor skills, and adjusts ratchet strip 58 having gears 59, to increase or decrease tension on the strap 30. The present design is also preferred over devices that use a string for pulling. Use of a string is counterproductive as it suggests to the user that the string should be pulled as opposed to an easier more efficient lifting of the lever of the present invention by use of multiple fingers or with the side of the hand or palm. Placing the indicator 53 on the lever, such as by painting or having a contrasting tip or end, informs the user that such end is the operations end of the lever that is to be lifted for the ratcheting operation. Indicator may also be of a glow-in-the dark variety.

A time indicator label 60 incorporated with the tourniquet is important since the label serves as a reminder to mark the time of application. If a tourniquet device is applied for greater than two hours, further medical complication may arise. In addition to operating as a reminder, label 60 provides a space for a user to actually record the time of day of the application. Recording such information is crucial in stressful situations where reference to time can be challenging or where individuals may enter into or out of consciousness or where assistants may come-and-go or may be distracted.

Tourniquet 20 is simple to operate in all conditions. Tourniquet 20 is designed to be operated in any environmental condition, day or night. Because a tourniquet may be utilized under combat conditions it might not be possible to operate the tourniquet visually. Large and tactile components such as lever 52 allow easy identification even without visual clues. Tourniquet 20 is easy to use under very stressful conditions, particularly where fine motor skills are impaired and only gross motor skill can be reliable.

Lever 52 has a distinct tactile feel. Lever 52 is easy to operate with cold fingers or even when wearing large bulky gloves. It also has indicator 53 with color coding to aid when visual cues may be utilized.

Distal end 34, and particularly tapered end 36 is made with a unique process to apply a polymer to the end of strap 30 which passes through buckle 40 on first stage tightening. This polymer application allows strap 30 to be a single thickness yet provide some degree of firmness to facilitate passage of tapered end 36 when utilized on an entrapped limb or self-application. This polymer is also color coded to add identification if visual cues are able to be used. If vision is not able to be used the polymer application to the tapered end 36 has a distinct tactile feel that aids in use.

The simple design combined with rugged components allows tourniquet 20 to survive the rigors of field use. The design and components of tourniquet 20 allow it to be carried in the field and also remain usable after prolonged storage. Designs that utilize compression bladders, elastic, or complicated mechanisms are prone to failure in the field environment and after prolonged storage.

Tourniquet 20 is very reliable due to the simple and rugged design. Ratchet assembly 50 is able to operate even when covered in blood, snow, dirt or sand. The large controls aid in operation under stressful conditions.

The simple design and components allow tourniquet 20 to be applied to one's self easily. There are no complex motions or components. Tourniquet 20 may be applied using only a single hand. This is critical if tourniquet 20 must be applied to one's self on an upper extremity.

Often a tourniquet must be applied to a limb that is entrapped or under an object. This entrapment prevents a closed loop type system from being placed on the limb. Tourniquet 20 is easily opened to allow strap 30 to be placed around an entrapped limb and then secured and tightened. As shown in FIG. 4 strap 30 may be fed through buckle 40. Strap 30 may also be removed from buckle 40 so that it may be slid underneath a trapped limb (i.e., leg) and then rethreaded once strap 30 encircles the limb. The specially tapered and sealed distal end 36 accommodates this use and threading. The polymer accommodates a low profile for efficient threading.

Prior to application of a tourniquet an operator preferably obtains specific training in the indications and proper application of a tourniquet. Tourniquet 20 should be carried in a location that is readily accessible to either hand of a user in an emergent situation. Prior to application of tourniquet 20 preferably all clothing and other material should be removed from the affected area. Tourniquet 20 should be placed around the injured limb. This is accomplished by placing the limb through loop 22 which is generally made of a strap of about 1.5 inch webbing (such as nylon webbing). Or, if the limb is entrapped the 1.5 inch webbing is removed from the 1.5 inch tension buckle 40, placed around the limb and rethread through the buckle 40. Different widths and lengths of webbing (strap 30) may be used.

Once tourniquet 20 is on the limb and placed above/proximal to the injury site, it should be tightened. This is done by pulling on the webbing (the tapered end tip is color coated polymer) which will pull the webbing (strap 30) through the buckle 40 and tighten around the limb. It is important to pull strap 30 as tight as possible. This will provided the first stage of compression and prepare the further tightening by the ratchet assembly 50.

Once strap 30 is tight ratchet assembly 50 may be utilized. Ratchet 51 having lever 52 as described above allows for the side of a hand or multiple fingers to grasp and lift lever 52. This lifting of lever 52 in an arch like manner will incrementally tighten strap 30 by drawing ratchet strip 58 through ratchet 51. This will effectively shorten the length of strap 30 and increase the circumferential pressure resulting in control of the bleeding.

Ratchet assembly 50 should be tightened until control of the bleeding has occurred. Once tourniquet 20 is tight the retainer wrap 70, such as velcro tabs, may be secured over lever 52 for added security. Once tourniquet 20 is applied the time of application should be documented on time tag 60.

Tourniquet 20 should not be covered once applied. The injured limb and tourniquet 20 should be re-assessed at regular intervals. A higher level of medical care should be sought immediately.

Tourniquet 20 may be removed or released by lifting release tab 55 and allowing ratchet strip 58 to retract which in turn loosens strap 30. Ratchet assembly 50 can then be reset by depressing release tab 55 and then reapplied as needed as described above.

While a specific embodiment of the invention will be shown and described in detail to illustrate the application of the principles of the invention, it will be understood that the invention may be embodied otherwise without departing from such principles. It is to be understood that the invention is not to be limited to the details herein given but may be modified within the scope of the appended claims.

What is claimed is:

1. A ratchet tourniquet for reducing arterial blood loss in an injured extremity, comprising:
    a buckle having an attachment portion and a feed portion;
    a strap having a proximal end and a distal end, said proximal end being attached to said buckle at said buckle attachment portion and said distal end feedable through said feed portion to form a constricting loop; and
    a ratchet assembly secured to said strap, said ratchet assembly comprising:
        a ratchet having a lever and a ratchet base, said ratchet base connected to said strap and having a base terminal end, said lever extending past said base terminal end; and
        a ratchet strip having ratchet gears and capable of being fed within said ratchet,
        said ratchet strip overlays a contiguous portion of said strap, said ratchet base and said ratchet strip connected to said contiguous portion of said strap where said lever includes an indicator positioned at a distal end of said lever.

2. The tourniquet of claim 1 where said distal end of said strap is tapered and sealed with a polymer.

3. The tourniquet of claim 2 where said polymer is an indicator.

4. The tourniquet of claim 1 where said indicator of said lever includes a color and where said distal end of said strap contains an indicator which includes a color which is the same as the color of said indicator of said lever.

5. The tourniquet of claim 1 further comprising a label attached to said ratchet assembly.

6. A ratchet tourniquet for reducing arterial blood loss in an injured extremity, comprising:
    a buckle having an attachment portion and a feed portion;
    a strap having a proximal end and a distal end, said proximal end being attached to said buckle at said buckle attachment portion and said distal end feedable through said feed portion to form a constricting loop; and
    a ratchet assembly secured to said strap, said ratchet assembly comprising:
        a ratchet having a lever and a ratchet base, said ratchet base connected to said strap and having a base terminal end which extends from a shoulder of said ratchet, said lever extending at least one-half inch past said shoulder such that a user may position more than one finger upon an underside of said lever when said lever is generally in a resting position; and
        a ratchet strip having ratchet gears and capable of being fed within said ratchet,
        said ratchet strip overlays a contiguous portion of said strap, said ratchet base and said ratchet strip connected to said contiguous portion of said strap.

7. A method of minimizing exsanguination comprising application of the tourniquet of claim 6 to a limb.

8. A ratchet tourniquet for reducing arterial blood loss in an injured extremity, comprising:
    a buckle having an attachment portion and a feed portion;
    a strap having a proximal end and a distal end, said proximal end being attached to said buckle at said buckle attachment portion and said distal end feedable through said feed portion to form a constricting loop; and
    a ratchet assembly secured to said strap, said ratchet assembly comprising:
        a ratchet having a lever containing a colored indicator positioned at a distal end of said lever; and
        a ratchet strip having ratchet gears and capable of being fed within said ratchet,
        said ratchet strip overlays a contiguous portion of said strap, said ratchet and said ratchet strip connected to said contiguous portion of said strap.

9. The tourniquet of claim 8 where said ratchet includes a shoulder from which a base end extends, said lever extends past said shoulder at least ½ inch when said lever is generally in a resting position.

10. The tourniquet of claim 8 where said ratchet includes a ratchet base having a terminal end, said lever extending past said base terminal end.

11. The tourniquet of claim 8 where said indicator is positioned at a terminal end of said distal end of said lever.

12. A ratchet tourniquet for reducing arterial blood loss in an injured extremity, comprising:
    a buckle having an attachment portion and a feed portion;
    a strap having a proximal end and a distal end, said proximal end being attached to said buckle at said buckle attachment portion and said distal end feedable through said feed portion to form a constricting loop; and
    a ratchet assembly secured to said strap, said ratchet assembly comprising:
        a ratchet having a lever and a ratchet base, said ratchet base connected to said strap, said lever extending at least one-half inch past a shoulder of said base such that a user may position more than one finger upon an underside of said lever when said lever is generally in a resting position; and
        a ratchet strip having ratchet gears and capable of being fed within said ratchet, said ratchet strip overlays a contiguous portion of said strap, said ratchet base and said ratchet strip connected to said contiguous portion of said strap.

* * * * *